United States Patent [19]

Schoenwald et al.

[11] Patent Number: 5,322,859

[45] Date of Patent: Jun. 21, 1994

[54] ANTIGLAUCOMA DRUG COMPOSITION AND METHOD

[75] Inventors: Ronald D. Schoenwald; Charles F. Barfknecht, both of Iowa City, Iowa

[73] Assignee: University of Iowa Research Foundation, Oakdale, Iowa

[21] Appl. No.: 14,801

[22] Filed: Feb. 8, 1993

[51] Int. Cl.$^5$ .......................................... A61K 31/135
[52] U.S. Cl. .................................. 514/649; 514/654; 514/913
[58] Field of Search ............... 514/649, 651, 654, 655, 514/912, 913

[56] References Cited

U.S. PATENT DOCUMENTS 4,820,737  4/1989  Schoenwald et al. ............... 514/654

OTHER PUBLICATIONS

Chiou, et al., "Ocular Hypotensive Actions of Serotonin Antagonist-Ketanserin Analogs", Journal of Ocular Pharmacology, vol. 8, No. 1, 1992.

Hurvitz, et al., "New Developments in the Drug Treatment of Glaucoma", Drugs 41(4) 514–532, 1991 [specifically pp. 521–525].

Primary Examiner—Zohreh Fay
Attorney, Agent, or Firm—Zarley, McKee, Thomte, Voorhees & Sease

[57] ABSTRACT

Use of sigma agonists as ophthlamic drugs for lowering intraocular pressure.

8 Claims, No Drawings

ANTIGLAUCOMA DRUG COMPOSITION AND METHOD

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive and some surgeons will use surgery only as a last resort.

Carbonic anhydrase inhibitors, prescribed orally, work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy much as tears wash the outside of the cornea.

In some middle-aged adults, fluids build up faster than can be absorbed back into the blood, for one of two reasons; the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness comes nausea, tingling in fingers and toes, and other side effects. Oral drugs generally do not, however, cause side effects in the eye.

Certain topical drugs, while causing less systemic effects, on the other hand, can cause severe headaches and constrict the pupil, making the daytime appear dark.

Many of our prior inventions have related to the effective use of topical carbonic anhydrase inhibitors. There are, however, many different mechanisms of inhibiting intraocular pressure, and therefore, effectively treating glaucoma. It, of course, goes without saying that clinicians desire to have a variety of drugs available, many of which work by different mechanisms, so that patients not susceptible to one type of drug, for example, perhaps not susceptible to carbonic anhydrase inhibitors or beta 2 blockers, such as Timilol, can still be effectively treated. Besides, beta 2 blockers and topical carbonic anhydrase inhibitors, there has been some efforts at using $\alpha_2$-adrenergic agonists, $\alpha_1$-adrenergic antagonists, dopamine agonists, and antagonists, prostaglandin analogs, D-timolol, cannabinoids and forskolin derivatives. Little attention has been paid to the effects of serotonin antagonists on the intraocular pressure (IOP) even though numerous neurotransmission agonists and antagonists have been tried, including cholinergic, adrenergic and dopaminergic systems. For a detailed view of various classes of drugs that might be used as antiglaucoma agents (see Ocular Hypertensive Actions of Serotonin Antagonists-Ketanserin Analogs, Chiou et al, *Journal of Ocular Pharmacology*, Vol. 8, No. 1, 1992).

It can therefore be seen that there is a continuing need for effective drugs which are both topical and which work by mechanisms other than beta 2 blockers and carbonic anhydrase inhibitors.

It is a primary objective of the present invention to provide effective drugs for lowing of intraocular pressure which will fill this need.

A further objective of the present invention is to provide a method of topical treatment which is effective for lowering intraocular pressure of glaucoma patients, which involves drug mechanisms other than carbonic anhydrase inhibition, and other than beta 2 blockers.

A further objective of the present invention is to provide drugs which can be effectively used topically because they have a high degree of solubility in tears and can effectively penetrate the cornea and release the pharmacologically active agent, without the need for systemic administration.

The method and manner of accomplishing each of the above objectives, as well as others, will become apparent from the detailed description of the invention which follows hereinafter.

SUMMARY OF THE INVENTION

The method of use of certain antiglaucoma drug treating effective compounds and ophthalmically active compositions thereof are disclosed. A particularly preferred compound is N,N-dimethyl-2-phenylethylamine and biologically acceptable salt forms thereof. This preferred compound, as well as others falling within the class below described, when placed in an ophthalmically acceptable pharmaceutical carrier and topically applied to the eye, effectively lower IOP.

DETAILED DESCRIPTION OF THE INVENTION

In its broadest sense, this invention provides certain compounds at dosage levels wherein they are ophthalmically active to effectively lower intraocular pressure. These compounds have never before been appreciated for their utility as ophthalmically effective intraocular pressure reducers, when topically applied to the eye. Compounds useful for this invention have the general formula:

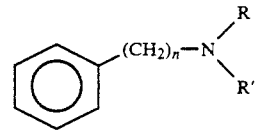

wherein n is 1,2, or 3, and R and R' are selected from the group consisting of $C_1$ to $C_6$ alkyl and cycloalkyl. It is most preferred that R=methyl or ethyl and that R' be selected from the group of methyl and hexyl and cyclohexyl. The most preferred compound is N,N-dimethyl-2-phenylethylamine and biologically acceptable salt forms thereof, wherein n=2, and R and R'=methyl. Salt forms of these compounds, wherein they are associated with pharmaceutically acceptable counter anions for the amines, such as halogen are perfectly acceptable. Other biologically active and acceptable salt forms of the compounds represented by the general formula above may of course be employed and are contemplated for use in this invention as long as they have the necessary organic structure to provide the ophthalmically active IOP effect, when topically administered, and, as long as they are they are still in a form which is pharmaceutically acceptable for topical administration, i.e. general solubility in acceptable pharmaceutical carriers.

The dosage may vary but is generally within the range of from 0.075% to 5% by weight volume basis, and preferably from 0.15% to 0.75% by weight volume basis. The amount of active compound within these ranges dissolved in suitable ophthalmically acceptable carriers have been demonstrated to effectively provide intraocular pressure lowering.

Suitable ophthalmically acceptable carriers are generally known and of course must be non-eye-irritating, non-toxic, and allow for safe, easy eye administration topically. Generally for this invention, aqueous-base systems wherein the carrier includes a buffer system to provide eye safe pH, a viscolyzer to provide suitable viscosity for eye comfort, an antibacterial agent, and a chemical preservative are adequate. The ophthalmically acceptable buffer should provide a composition having a pH within the range of about 5.5 to about 7.8, preferably from about 6.8 to about 7.4. Suitable ophthalmically acceptable buffers can be selected from the water soluble salt forms of citrate, borate, phosphate, carbonate, and acetate.

The viscolyzer suitable for use in this invention should provide the composition with a viscosity within the range of from about 4 centipoises to about 100 centipoises, preferably from about 5 centipoises to about 35 centipoises. Suitable viscolyzers can be selected from the group consisting of hydroxyethylcellulose, hydroxypropyl methylcellulose, methylcellulose and a polyacrylamide sold under the trade name GELAMIDE 250 by American Cyanamide.

In addition, the ophthalmic composition ideally will include antibacterials to provide safety and efficacy for storage stability. The amount of antibacterial can be within the range of from about 0.005% to about 0.2% by weight/volume of the composition. A suitable antibacterial would include, for example, from about 0.005% to about 0.2% by weight/volume of benzalkonium chloride, from about 0.25% to about 0.5% of chlorobutanol, about 0.1% of thimerosal, about 0.05% methylparaben, about 0.001% propylparaben, and sodium chloride in an amount sufficient to make an isotonic solution.

Finally, chemical preservatives may also be used, for example sodium thiosulfate at about a 0.3% level and ethylenediaminetetraacetic acid at about 0.005%. It goes without saying that the precise ophthalmic carrier must be selected to provide pharmaceutical elegance, to provide eye comfort and to allow for effective topical administration. Formulation of such is well within the skill of the ordinary artisan who prepares ophthalmic carrier compositions.

As heretofore mentioned, the most preferred is N,N-dimethyl-2-phenylethylamine. This compound has previously been disclosed by the applicants as an ophthalmically effective tear stimulant to induce the eye to naturally produce tears, however, the most preferred and active dose ranges have been found to be lower than the amount required for IOP reduction, namely, the amount disclosed as preferred in our prior patent (U.S. Pat. No. 4,820,737) is 0.2% to about 0.6% by weight volume basis. Moreover, there is no disclosure in that patent, of any use of this compound for IOP lowering action.

As demonstrated by the examples below, the active compounds here claimed, are receptor selective for serotonin 1 receptor, serotonin 2 receptor, and alpha 2 receptor. It is therefore clear that these compounds are functioning to lower IOP by a mechanism other than beta 2 blocking and carbonic anhydrase inhibition. While applicant does not wish to be bound by any theory of operability, it would appear that the compounds are serotonin 1 and 2 and alpha 2 receptor antagonists, when used at the dosage levels expressed herein, and for that reason, function effectively for lowering IOP.

The following examples are offered to further illustrate, but not limit, the invention. The first example shows preparation of the most preferred compound following within the scope of the general formula for the active compounds of this invention. As can be seen, the organic synthesis is conventional. The second example shows the compounds are effective serotonin 1, 2, and alpha 2 receptor agonists. The third example shows effective lowering of IOP for rabbit eyes, which are known to correlate and closely parallel and predict human eye activity.

EXAMPLE 1

N,N-dimethyl-2-phenylethylamine hydrochloride

2-Phenylethyl bromide [0.01 mol.] and dimethylamine hydrochloride [0.02 mol.] are stirred at room temperature [24 hrs] and then refluxed [1 hr.] with potassium carbonate [0.06 in methanol. The insoluble materials are filtered and the solution evaporated and distilled to form N,N-dimethyl-2-phenylethylamine. The hydrochloride salt [m.p. 163-4° C.] is formed and recrystalized from ethanol. The structure was confirmed by its proton nmr spectrum, by its chemical ionization mass spectrum, and its correct elemental analyses.

EXAMPLE 2

N-cyclohexyl-N-methyl-2-phenylethylamine

The preparation of N-cyclohexyl-N-methyl-2-phenylethylamine was accomplished in the following manner. This was prepared by treating a suspension of N-methyl- cyclohexylamine (1.98 ml, 0.015 moles, 1.70 g) and potassium carbonate (4.15 g, 0.03 moles, 2 eq.) in 4-methyl-2-pentanone (50 ml) with phenethylbromide (2.05 ml, 0.015 moles, 2.78 g). The reaction was heated under reflux 16 hours. The insoluble material was removed by a hot gravity filtration and the filtrate was concentrated in vacuo on the rotary evaporator. The resulting oil was flash chromatographed on davisil 633 using 20% ethyl acetate/hexane as the eluent. The appropriate fractions were pooled and concentrated. The oil was dissolved in ether and treated with HCl gas. The resulting precipitate was collected by vacuum filtration and recrystalized from absolute ethanol. m.p. 187°-188° C. EI Mass Spec. M+217(0.9), 126(92.2), 113(4.5), 112(1.2), 105(6.9), 91(32.2), 83(9.8), 77(11.6), 70(66.0), 65(15.9), 57(26.0), 55(39.8), 53(8.6), 45(2.8), 44(100), 43(8.2), 42(42.2), 41(34.9).

EXAMPLE 3

Preparation of N-cyclohexyl-N-ethyl 2-phenylethylamine hydrochloride

Into a 250 ml. round bottom flask fitted with a water cooled condenser and magnetic spin bar the following reagents were placed: N-ethyl-cyclohexylamine [3.82 g., 0.03 moles], potassium carbonate [6.8 g., 0.05 moles], 4-methyl-2-pentanone [100 ml.] and 2-phenylethyl bromide [5.55 g., 0.03 moles]. The combined reagents were stirred magnetically, while being heated to reflux, overnight. The solvent was removed by vacuum distillation to yield a brown oil. The product was purified by flash chromatography on silica gel using 10% ethyl acetate in hexane as the eluting solvent system. The product fractions from the chromatographic separation were combined and the solvent removed by vacuum distillation to yield a light yellow oil. The yellow oil was dissolved in anhydrous diethyl ether and hydrogen chloride gas was introduced to form a white hydrochloride salt. The hydrochloride salt was recrystallized from absolute ethanol to form a hygroscopic solid, m.o. 126° C. The nmr and ms analysis was consistent with the assigned structure.

EXAMPLE 4

Bioreceptor results

A number of compounds were sent to NovaScreen ® (5200 Freeport Centre, Baltimore, Md. 21224) to determine the compounds' receptor selectivity. A summary of the most significant binding relative to lowering of IOP is presented in the table below. Compounds which show inhibition in the range of 20% to 49% at an assay concentration of 10 μM are marginally active and do not warrant further examination. Compounds which show inhibition of 50% or greater at an assay concentration of 10 μM to 1 nM are considered active or very potent, respectively. In the table below a number of compounds show significant results for two or more of the significant receptors.

TABLE 1

| | % INHIBITION* | | |
|---|---|---|---|
| Cpd | $10^{-9}$M 1 nM | $10^{-7}$M 100 nM | $10^{-5}$M 10 μM |
| Serotonin 1 Receptor | | | |
| n = 2, R&R' = CH$_3$ | 62.3 | 70.6 | 82.3 |
| n = 2, R = CH$_3$, R' = n-hexyl | 10.3 | 30.0 | 55.0 |
| n = 1, R = CH$_3$, R' = C$_2$H$_5$ | 5.7 | 6.2 | 17.2 |
| n = 2, R = C$_2$H$_5$, R' = cyclohexyl | 2.6 | −4.0 | 12.2 |
| N = 3, R = methyl, R' = cyclohexyl | −6.3 | −10.2 | 5.7 |
| Serotonin 2 Receptor | | | |
| n = 2, R&R' = CH$_3$ | −2.1 | 10.7 | 46.9 |
| n = 2, R = CH$_3$, R' = n-hexyl | 2.3 | 9.6 | 92.0 |
| n = 2, R = C$_2$H$_5$, R' = cyclohexyl | −11.2 | 4.7 | 48.9 |
| n = 3, R = methyl, R' = cyclohexyl | −15.4 | −8.0 | 82.1 |
| Alpha 2 Receptor | | | |
| n = 2, R&R' = CH$_3$ | 8.1 | 15.3 | 96.7 |
| n = 2, R = CH$_3$, R' = n-hexyl | 1.6 | 6.7 | 95.7 |
| n = 1, R = CH$_3$, R' = C$_2$H$_5$ | 2.2 | 4.7 | 53.0 |
| n = 3, R = methyl, R' = cyclohexyl | 3.3 | 9.3 | 81.0 |

*no activity = less than 20% at 10 μM
*marginal activity = 20–49% inhibition at 10 μM
*active compound = 50–100% inhibition at 10 μM
*very potent compound = 50–100% inhibition at 1 nM The above five mentioned compounds are the most preferred compounds of the present invention, with N,N-dimethyl-2-phenylethylamine being most preferred.

EXAMPLE 5

IOP Lowering results Procedure

The "IOP recovery rate assay" as reported by Vareilles and Lotti (Ophthalmic Res., 13, 72–79, 1981) is used.

IOP was measured at 15, 25, 35, 45, 60, 75, 90 and 120 minutes with an applanation pneumatometer (Digilab Model D). Fifty uL of a 0.6% solution of N,N'-dimethyl-2-phenylethylamine containing a pH 7.4 phosphate buffer was administered topically to the right eye 60 minutes before the start of the sodium chloride infusion. Control animals were given vehicle without drug.

The hypertonic sodium chloride solution causes a temporary decline in IOP which returns to normal IOP in about 90 minutes if no drug is administered. IOP gradually returns to normal at a constant rate buy more slowly if the in vivo secretion rate of aqueous humor is reduced due to the presence of drug. The return to normal IOP is measured from the positive linear slope which is a measure of the constant rate of return to normal IOP and begins at about 30–45 minutes after starting the NaCl infusion. A comparison of the slope with and without the addition of N=2, R&R'=CH$_3$ to the rabbit eye is expressed as "% reduction".

RESULTS

The average (±standard deviation) slope values for 12 rabbit eyes was:

| | |
|---|---|
| rabbit eye (n = 12) given vehicle only = | 0.109 ± 0.0268 |
| rabbit eye (n = 12) given 0.6% of N = 2, R&R' = CH3 | 0.066 ± 0.027 |
| % Reduction = 38.5% | |

The results indicate that N=2, R&R'=CH$_3$ is a potent in vivo antiglaucoma drug.

From the above examples, it can be seen that the invention accomplishes at least all of its stated objectives.

What is claimed is:

1. A method for treating elevated intraocular pressure which comprises;
   topically applying to an affected eye an intraocular pressure lowering effective amount of a compound of the formula:

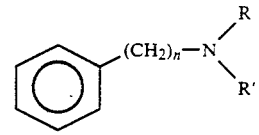

wherein n is 1, 2, or 3, and R and R' are selected from the group consisting of C$_1$–C$_6$ alkyl and C$_3$–C$_6$ cycloalkyl.

2. The method of claim 1 wherein n=2, and R and R' are methyl.

3. The method of claim 1 wherein n=1, and R is methyl, and R' is ethyl.

4. The method of claim 1 wherein n=2, and R is methyl, and R' is normal hexyl.

5. The method of claim 1 wherein n=2, R is ethyl, and R' is cyclohexyl.

6. The method of claim 1 wherein n=3, R is methyl, and R' is cyclohexyl.

7. The method of claim 1 wherein the dosage of the active compound of the above formula is from 0.075% on a weight volume basis to about 5% on a weight volume basis on topical composition.

8. The method of claim 1 wherein the dosage of the active compound of the above formula is from 0.15% on a weight volume basis to about 0.75% on a weight volume basis on topical composition.

* * * * *